United States Patent [19]

Feinstein et al.

[11] 4,172,813

[45] Oct. 30, 1979

[54] PROCESS FOR SELECTIVELY HYDRODEALKYLATING/TRANSALKYLATING HEAVY REFORMATE

[75] Inventors: Allen I. Feinstein, Wheaton, Ill.; Ralph J. Bertolacini, Chesterton, Ind.

[73] Assignee: Standard Oil Company (Indiana), Chicago, Ill.

[21] Appl. No.: 849,594

[22] Filed: Nov. 8, 1977

[51] Int. Cl.² .......................... C07C 3/58; C10G 37/04
[52] U.S. Cl. ...................................... 585/475; 208/111; 208/92; 252/455 Z; 585/489; 585/752
[58] Field of Search ........................... 208/92, 64, 111; 260/672 T

[56] References Cited

U.S. PATENT DOCUMENTS

| | | | |
|---|---|---|---|
| 3,677,973 | 7/1972 | Mitsche et al. | 252/455 Z |
| 3,780,121 | 12/1973 | Suggitt et al. | 260/672 T |
| 3,862,254 | 1/1975 | Eisenlohr et al. | 260/674 SE |
| 3,957,621 | 5/1976 | Bonacci et al. | 208/60 |

Primary Examiner—Herbert Levine
Attorney, Agent, or Firm—William C. Clarke; Arthur G. Gilkes; William T. McClain

[57] ABSTRACT

Fractionated heavy reformate containing ethyltoluenes and propylbenzenes is selectively hydrodealkylated and transalkylated to produce ethylbenzene-lean xylenes, benzene and $C_2$-$C_4$ paraffins in the presence of a catalyst comprising a tungsten/molybdenum component of $WO_3$ and $MoO_3$ and an acidic component of 60 (wt)% of mordenite and 40 (wt)% of catalytically active alumina.

11 Claims, 1 Drawing Figure

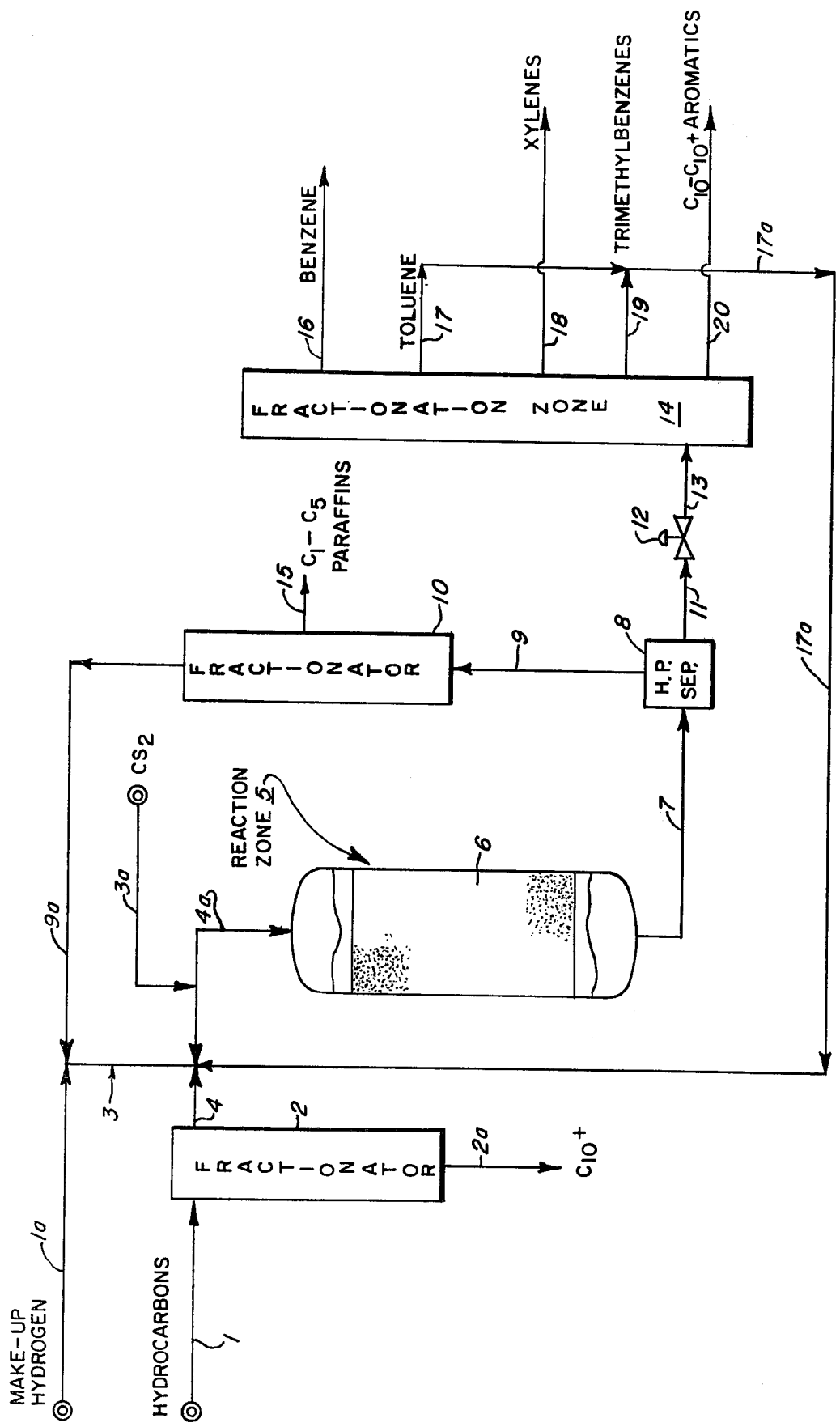

PROCESS FOR SELECTIVELY HYDRODEALKYLATING/TRANSALKYLATING HEAVY REFORMATE

BACKGROUND OF THE INVENTION

This invention relates to a method for the selective hydrodealkylation and transalkylation of aromatic hydrocarbons. Alkyl aromatic compounds have long been produced from hydrocarbon fractions relatively rich in such materials. Early sources were liquids from cooking or other distillation of coals. More recently, these products have been derived from fractions obtained in refining of petroleum. An important source in recent years has been the aromatic liquid naphthas resulting from the thermal cracking of gases and naphthas to produce olefins.

However, derived, these aromatic-rich streams containing a broad range of components have usually been distilled and otherwise separated (e.g., solvent extraction) to obtain the desired product components. The purpose of these operations typically has been to obtain para-xylene and benzene which are now used in huge quantities in the manufacture of terephthalic acid and other chemical products. The separated streams resulting from the above separation by distillation or other means accordingly consist of product streams of benzene, toluene, $C_8$ aromatics containing xylenes and a bottoms product of $C_9$ and $C_{10}+$ aromatics. The $C_9$ component can be separated by means of distillation and can be a source material for manufacture of lighter aromatic hydrocarbons by hydrocracking but with some attendant material losses. The $C_{10}$ component is useful for heavy solvents and gasoline.

The presence of ethylbenzene in mixed xylenes is detrimental to process yields and process economics when these xylenes are utilized in the production of p-xylene. Fractional distillation to remove ethylbenzene from mixed xylenes is not economically practical because of the closeness of their boiling points. Ethylbenzene can be removed from xylenes by repeated recrystallizations but this is economically very expensive and is technically difficult.

This invention relates to a conversion process for the selective hydrodealkylation and transalkylation of fractionated heavy reformate containing ethyltoluenes and propylbenzenes into more useful compounds. More specifically, this invention is concerned with a conversion process for the concurrent transalkylation and hydrodealkylation of a fractionated heavy reformate stream containing ethyltoluenes and propylbenzenes to produce ethylbenzene-lean xylenes, benzene, and $C_2-C_4$ paraffins without hydrodealkylating the trimethylbenzenes, toluene or xylenes, utilizing a catalyst comprising a tungsten/molybdenum component of $WO_3$ and $MoO_3$ and an acidic catalyst of 60 (wt)% mordenite and 40 (wt)% catalytically active alumina. Fractionated heavy reformates are reformates from which $C_8$ aromatics and lighter components have been largely removed.

In the prior art, methods which have been used to produce aromatic chemicals from fractionated heavy reformates utilize a hydrocracking or hydrodealkylation step to convert the $C_9$ and $C_{10}+$ aromatic components to benzene, toluene and $C_8$ aromatics. The $C_6+$ paraffins are converted into readily distillable low boiling hydrocarbons of $C_5$ and lighter. Processes utilizing this principle are described in U.S. Pat. Nos. 3,957,621 and 3,862,254. However, there is no teaching in the prior art that ethylbenzene-lean xylenes, benzene and $C_2-C_4$ paraffins can be produced from fractionated heavy reformate in the presence of a catalyst comprising a tungsten/molybdenum component of $WO_3$ and $MoO_3$ and an acidic cracking component of 60 (wt)% of mordenite and 40 (wt)% of catalytically active alumina without a separate hydrocracking step. A high yield of xylenes is accordingly obtained from $C_9$ aromatics as large losses to benzene and toluene are not incurred via hydrocracking. A high yield of $C_2-C_4$ paraffins is obtained from the hydrodealkylation of the alkyl aromatics.

Although the transalkylation of toluene and trimethylbenzenes has been widely studied (U.S. Pat. Nos. 3,260,764; 3,527,825; 3,677,973) because of the demand for greater quantities of high purity aromatic hydrocarbons, the results of such studies have not been sufficient to cause supplies of these hydrocarbons to increase sufficiently to meet this demand. One of the sources of $C_9$ aromatics can be the heavy reformate stream; however, the trimethylbenzene concentration in heavy-reformate derived $C_9$ aromatics often is only 50-60%. The remaining $C_9$ aromatics content can consist of 35-42% ethyltoluenes and 6-10% propylbenzenes and indane. The presence of ethyltoluenes in a transalkylation reaction feed can have a detrimental effect on both xylene yield and quality, because they would contribute to the formation of ethylxylenes and ethylbenzenes. Equilibrium calculations, based on free energy data, indicate that if heavy-reformate derived $C_9$ aromatics are used in a transalkylation reaction with toluene, the resulting product will contain as much as 6% ethylxylenes and as much as 13% ethylbenzene in the $C_8$ aromatics. Accordingly, a process using heavy-reformate derived aromatics feedstock requires a dual-function catalyst, one that possesses deethylation as well as transalkylation capability.

Typical of the prior art on hydrodealkylation of alkyl aromatics are the following:

U.S. Pat. No. 2,422,673 teaches hydrodealkylation or demethylation of an alkyl aromatic using a catalyst containing nickel or cobalt on diatomaceous earth. Temperatures used in the process are between 350°–650° F. and pressures are between subatmospheric to 1000 psig. The reaction is carried out at a low pressure of hydrogen so as to obtain a high proportion of demethylation and a relatively small amount of hydrogenation of aromatic hydrocarbons to naphthenic hydrocarbons.

U.S. Pat. No. 2,734,929 discloses hydrodealkylation of alkyl aromatics, including a process for removing methyl groups which are attached directly to the benzene ring, which methyl groups are more difficult to remove than splitting a longer-chained alkyl group down to a methyl group or removing the longer-chained alkyl group entirely. Examples are toluene and xylene with benzene and toluene resulting respectively. Selective dealkylation of ethylbenzene, m-xylene and p-xylene is disclosed, ethylbenzene being the most readily dealkylated, meta-xylene next and para-xylene the least. The patent teaches that alkyl groups in excess of a single methyl group on the benzene ring are much more easily removed than the last methyl group. According to the patent, the catalyst used contains a Group VI-B or Group VIII metal hydrogenation component such as chromium, molybdenum, tungsten, uranium, iron, cobalt, ruthenium, rhodium, palladium, osmium, iridium and platinum, platinum being the least preferred. The hydrogenation catalyst is preferably suspended on a carrier such as alumina, silica gel, zirconia, thoria, magnesia, titania, montmorillonite clay, bauxite, diatomaceous earth, crushed porcelain. The alumina carrier can also contain some silica. Operating conditions include a temperature between 900°–1200° F. at a pressure of 150–2000 psig.

U.S. Pat. No. 3,478,120 discloses a process for selective hydrodealkylation of ethylbenzene to toluene, benzene, methane and ethane with the hydrodealkylation being carried out in the presence of xylenes. The catalyst used comprises an iron group metal on calcium aluminate. Operating conditions include a temperature range of 500°–1200° F. pressure from atmospheric to 2000 psig.

Accordingly, it is well known in the prior art to hydrodealkylate and/or hydroisomerize alkyl aromatics but concurrent selective hydrodealkylation and transalkylation of ethyltoluene and propylbenzene streams into ethylbenzene-lean xylenes, benzene and paraffins without hydrode-methylating the trimethylbenzenes, toluene or xylenes also present in the stream has not been known.

SUMMARY OF THE INVENTION

A hydrodealkylation/transalkylation process for selectively hydrodealkylating ethyltoluenes and propylbenzenes and transalkylating toluene and polyalkylbenzenes to ethylbenzene-lean xylenes, benzene and $C_2$–$C_4$ paraffins which process comprises contacting the feedstock with a catalyst comprising tungsten/molybdenum components on a mordenite base suspended in a matrix of a refractory inorganic oxide at a temperature in the range from about 600° to 1000° F. and a pressure of from about 150 to 500 psig.

DETAILED DESCRIPTION OF THE INVENTION

The process of this invention is a process for the selective hydrodealkylation and transalkylation of petroleum hydrocarbons. Particularly, it is a process for the hydrodealkylation and transalkylation of alkyl aromatic hydrocarbons wherein alkyl groups of two carbons and more are dealkylated and alkyl groups of one carbon are transferred from one molecule to another. Among the resulting products is a $C_2$–$C_4$ paraffin stream which is typically a desirable feed for an olefin plant.

The success of this hydrodealkylation/transalkylation process is due primarily to the use of particular catalytic compositions which are employed therein and the operating conditions that are used.

Typical feedstocks of the present invention are petroleum hydrocarbon streams which contain single-ring aromatic hydrocarbons which boil below about 350° F. and contain 7–10 carbon atoms. Such aromatic hydrocarbon streams can be a petroleum hydrocarbon fraction derived from petroleum reformate and which is known as heavy reformate. For purposes of this invention, the term "heavy reformate" is defined as the heavy fraction obtained from a catalytic reformer with a boiling point range of 300° F. to 430° F. comprising $C_9$ aromatics, $C_{10}$ aromatics and heavier components. Fractionated heavy reformate is defined as that fraction of heavy reformate from which the $C_{10}$'s and heavier components have been largely removed, leaving typically only $C_9$ aromatics. Accordingly the feedstock of this invention can contain ethyltoluenes, propylbenzenes, trimethylbenzenes and indane.

Typically the feedstock is mixed with a hydrogen-containing gas and preheated to a suitable temperature, and then transferred to the hydrode-alkylation/transalkylation reaction zone, which may contain one or more reactors. Advantageously, the feed is substantially completely vaporized before being introduced into the reaction zone.

The feedstock is contacted in the reaction zone with the hereinafter described catalyst in the presence of a hydrogen-affording gas. Advantageously, a hydrogen-to-hydrocarbon mole ratio of at least 4:1 is employed, and the hydrogen-to-hydrocarbon mole ratio can range up to 20:1. Preferably, the hydrogen-to-hydrocarbon mole ratio can range between 5:1 to about 9:1 at pressures of 150 to 250 psig respectively. Contact time can range from 1 to 20 seconds, preferably 3 to 10 seconds. Contact time is defined as bulk volume of the catalyst divided by volumetric flow rate of reactants and hydrogen. Other operating conditions comprise an elevated temperature of about 600° F. to about 1000° F. preferably about 800° F. to about 900° F.; an elevated pressure of about 100 psig to about 500 psig, preferably about 170 psig to about 250 psig; and WHSV of about 0.1 to about 20 weights of hydrocarbon per hour per weight of catalyst, preferably about 1 to about 10 weights of hydrocarbon per hour per weight of catalyst.

Side reactions such as hydrogenation of the aromatic ring are controlled by the sulfiding of the catalyst to the sulfided form with sulfur compounds, such as hydrogen sulfide and carbon disulfide, either prior to or at the start of the hydrodealkylation/transalkylation reaction. If hydrogen sulfide is used, the catalyst is advantageously subjected to the hydrogen sulfide prior to its use as a catalyst for hydroadealkylation/transalkylation. If carbon disulfide is employed, it may be added to the hydrocarbon feed during the initial stages of the run.

In the process of this invention, it has been determined that toluene is not a necessary element in the fresh feed to the process. However, toluene in equilibrium amounts is produced in situ from the ethyltoluene in the feed during the course of the reaction. The recycle of this toluene maintains the necessary toluene equilibrium. If required, toluene can be recovered as a product. Toluene can also be admixed with reformate $C_9$ aromatics as the fresh feed to the process.

The catalytic composition of the process of this invention comprises a hydrogenation component disposed upon a solid acidic cracking support. The hydrogenation component comprises two members selected from the group consisting of the oxides of metals of Group VIb of the Periodic Table of Elements and mixtures thereof. The pertinent Periodic Table of Elements may be found on the inside of the back cover of HANDBOOK OF CHEMISTRY AND PHYSICS, 45th edition, Robert C. Weast, editor, Chemical Rubber Company, Cleveland, Ohio (1964). The preferred Group VIb metals are tungsten and molybdenum. Molybdenum is present in an amount within the range of about 1.0 to about 20 weight percent, expressed as $MoO_3$ and based upon the weight of the catalytic composition, while tungsten is present in an amount within the range of about 1 to about 10 weight percent, expressed as $WO_3$ and based upon the weight of the catalytic composition.

The solid acidic cracking support of the catalyst employed in the process of the present invention comprises a mordenite-type, large-pore crystalline aluminosilicate material and a suitable refractory inorganic oxide. Preferably, the mordenite-type, large-pore crystalline aluminosilicate material is suspended in and distributed throughout the matrix of the refractory inorganic oxide. The mordenite-type, large-pore crystalline aluminosilicate material is present in an amount within the range of about 5 to about 95 weight percent, based upon the weight of the support.

The refractory inorganic oxide component of the support of the catalyst that is employed in the process of the present invention may be an oxide of a single metal, or it may be a mixture of the oxides of two or more metals of Groups III and IV of the Periodic Table of Elements. For example, the refractory inorganic oxide component may be catalytically active alumina, or it may be a mixture of silica and alumina, or it may be a mixture of boria, titania, gallia, and alumina. The preferred refractory inorganic oxide is a catalytically active alumina.

An example of the refractory inorganic oxide component that is employed in the catalyst of this invention is PHF or Aero-1000 Alumina manufactured by American Cyanamid Corp. It is described as a high-purity gamma-alumina, the inspection data being: surface area 206 $m^2/g$, pore volume 0.6 cc/g, average pore diameter 90 Å (Angstroms), sodium content 0.1 wt. %, silicon content 0.02 wt. %, iron content 0.025 wt. %.

The aluminosilicate material that is a component of the support of the catalytic composition that is employed in the process of the present invention is a mordenite-type, large-pore crystalline aluminosilicate material. It is sometimes hereinafter referred to as "mordenite aluminosilicate material." By large pore material is meant a material that has pores which are sufficiently large to permit the passage thereinto of benzene molecules and larger molecules, and the passage therefrom of reaction products. For use in catalysts that are employed in petroleum hydrocarbon conversion process, it is preferred to employ a large-pore crystalline aluminosilicate material having a pore size of at least 6 to 10 Angstrom units (Å). The mordenite aluminosilicate material of the catalyst of the present invention possesses a pore size of 6-9 Å.

A preferred mordenite-type aluminosilicate material is the synthetic Zeolon manufactured by the Norton Chemical Company. Zeolon-H is the hydrogen form of this synthetic mordenite. Mordenite is characterized by its high silica-to-alumina ratio and its crystal structure. The mordenite may have a silica-to-alumina ratio within the range of about 6 to about 100. The composition of mordenite is given in Kirk-Othmer, "Encyclopedia of Chemical Technology," first edition, Volume 12, page 297 (1954), as $(Ca, Na_2)Al_2Si_9O_{22}.6H_2O$. The proposed structure is one in which the basic building block is a tetrahedron consisting of 1 silicon or aluminum atom surrounded by four oxygen atoms. The crystal structure is made up of 4- or 5-membered rings of these tetrahedra. These 4- and 5-membered rings are believed to give the structure its stability. The chains are linked together to form a network having a system of large parallel channels interconnected by small cross channels. Rings of 12 tetrahedra form the large channels. Other synthetic zeolites also have such 12-membered rings, but they have interconnected cages, whereas the mordenite has parallel channels of uniform diameter. For example, synthetic faujasite, which has the formula $Na_3Al_3Si_4O_{14}$, is characterized by a 3-dimensional array of pores which consist of 12–13 Angstrom (Å) cages interconnected through 6–9 Å windows.

The mordenite aluminosilicate material that is preferred, the Zeolon manufactured by the Norton Chemical Company, with its high ratio of silica to alumina exhibits the ability to undergo complete acid exchange from the original sodium form to the hydrogen form. The theoretical silica-to-alumina ratio is about 10 to 1 and the effective pore diameter in Angstroms (Å) is within the range of 6 to 9 Å. The surface area in square meters/gram is within the range of 400–450 $m^2/g$ and its static water capacity in weight percent is within the range of 10–11%.

The mordenite in the catalytic composition of the present invention may be in the unexchanged cation form containing exchangeable sodium and/or calcium ions, or other alkali metal or alkaline earth metal ions. Preferably, the alkali metal cations, such as sodium ions, may be replaced or cation-exchanged with a member selected from the group consisting of an alkaline earth metal, a rare earth metal, hydrogen, and a hydrogen precursor to provide an alkali metal content in the mordenite that is less than 1 weight percent, calculated as the metal. Ammonium ions comprise a hydrogen precursor and may be employed to cation-exchange the alkali metal of the mordenite. Heat is employed to drive off ammonia leaving the mordenite in the hydrogen form. Mordenite differs from other aluminosilicates in that substantially all the exchangeable metal cations may be replaced with hydrogen ions without causing destruction of the characteristic crystal structure of the mordenite.

The porous refractory inorganic oxide that is employed in the catalytic composition of the present invention may be a catalytically active alumina, silica-alumina, silica-magnesia, titania-alumina, zinc-oxide-alumina, gallium oxide-alumina and the like. Catalytically active alumina, such as gamma-alumina and eta-alumina, is the preferred refractory inorganic oxide. Such alumina should have a pore diameter of about 70 Angstroms to about 200 Angstroms and a surface area of at least 100 square meters per gram. Suitably, the surface area should be within the range of about 200 square meters per gram to about 500 square meters per gram.

The co-catalytic composition of the present invention may be prepared in various ways. For example, finely divided mordenite-type aluminosilicate material may be stirred into a sol or gel of the refractory inorganic oxide and soluble compounds of the Group VIb metals added to the sol or gel, followed by the cogelling of the sol or gel mixture by the addition of dilute ammonia. The resulting cogelled material is then dried and calcined. In another method of preparation, the finely divided mordenite is mixed into a sol or gel of the refractory inorganic oxide, the sol or gel mixture is cogelled by the addition of dilute ammonia and the resulting gel is subsequently dried, pelleted, calcined, cooled, and impregnated with a solution or solutions of the Group VIb metals. As an alternate method of preparation, a hydrogel of the refractory inorganic oxide is blended with finely divided aluminosilicate material, and a solution or solutions of soluble compounds of the Group VIb metals are added to this blend, and the resulting mixture is thoroughly blended. The blended mixture is then dried, pelleted, and calcined. Suitably drying conditions for use in the above described metal manufacturing methods comprise a temperature in the range of about 200° F. to about 400° F. and a drying time of about 5 to 30 hours. Suitable calcination conditions comprise a temperature in the range of about 900° to 1400° F. and a calcination time of about 2 to about 20 hours. Preferred drying and calcination conditions are a temperature of about 250° F. for about 16 hours and a temperature of about 1000° F. for about 6 hours, respectively.

The catalytic composition that is employed in the process of the present invention can be prepared in several other ways. For example, the mordenite-type, large-pore crystalline aluminosilicate material can be pulverized into a finely-divided state and then physically admixed with a finely-divided powder of the selected refractory inorganic oxide component. After a thorough blending of the two solid components, the resulting mixture may be co-pelleted, and impregnated with one or more solutions of the metals of the hydrogenation component, i.e., the metals of Group IVb. The resulting composition is thoroughly mixed to form a blended composition, which is subsequently dried to a moisture content ranging from about 20 to 40 weight percent, based upon the total weight of the composition. The dried material is then calcined at a temperature within the range of about 900° to about 1100° F.

The following is another method of preparation. The mordenite-type, large-pore crystalline aluminosilicate material in a finely-divided state may be added to a hydrosol or a hydrogel of the refractory inorganic oxide component and blended therein to form a homogenous mixture. The hydrogenation component, i.e., the metals of Group VIb, are added in the form of heat-decomposable components to this homogenous mixture. These heat-decomposable components may be added in a single solution or in several solutions. The resulting composition is then thoroughly mixed, dried, and calcined, as described above.

Alternatively, the homogenous mixture of the above paragraph may be dried and pelleted, or dried, and the resulting material may be impregnated with the hydrogenation component, followed by drying and calcining, as described above.

The invention comprises a process for the hydrodealkylation/transalkylation of alkylaromatics which process consists essentially of contacting an alkylaromatic stream in a reaction zone under hydrodealkylation/transformation conditions and in the presence of a catalyst to furnish a product containing hydrodealkylated/transalkylated aromatics, said catalyst comprising a hydrogenation component which comprises two Group VIb metals deposed upon a solid support of a co-catalytic component comprising H-mordenite and a porous refractory inorganic oxide, said refractory inorganic oxide being selected from the group consisting of catalytically active alumina or silica-alumina, silica, zirconia, gallium oxide, titania and mixtures thereof, and said Group VIb metals being present as members selected from the group consisting of (1) the elements, (2) their oxides, (3) their sulfides, and (4) mixtures thereof. When the refractory inorganic oxide is alumina, the catalyst co-support contains at least 5 weight % alumina, preferably 80 weight % alumina. The process of this invention will be understood from the following description and examples.

PROCESS DESCRIPTION

A simplified process flow scheme for this embodiment is depicted in the FIGURE. Auxiliary equipment, such as pumps and heat exchangers, is not shown in the drawing. Such auxiliary equipment is well-known to those skilled in the art and the uses and locations of this equipment in this particular process system will be recognized easily by those having ordinary skill in the art.

Fresh feedstock comprising heavy reformate is introduced into the process system by way of line 1 and fractionated in fractionator 2. $C_9$ hydrocarbons as overhead in line 4 are removed and the $C_{10}$ or $C_{10}+$ fractions are taken as bottoms in line 2a. Make-up hydrogen is introduced by way of line 1a. Hydrogen-containing gas from lines 1a and 9a is introduced into the $C_9$ hydrogen stream by way of line 3. Carbon disulfide is added by way of line 3a. The resulting mixture with recycle gas from line 9a is passed through line 4a into reaction zone 5. Reaction zone 5 contains a catalyst bed or catalyst beds 6. The catalyst in this reaction zone comprises 3.0 percent by weight $WO_3$ and 5 weight percent by weight $MoO_3$ on a co-catalytic support comprising 60 percent by weight H-mordenite, large-pore crystalline aluminosilicate material suspended in a matrix of catalytically active alumina.

The effluent from reaction zone 5 is passed through line 7 to high pressure separator 8 wherein the light gases containing hydrogen are separated therefrom. The separated hydrogen-containing gas is passed through lines 9 and 9a to line 3 to be recycled to reaction zone 5. The low-boiling alkanes which consist mainly of $C_1$–$C_5$ paraffins are separated in fractionator 10 at this point and removed by line 15. Make-up hydrogen is added to this hydrogen-containing gas by way of line 1a. The liquid effluent from high pressure separator 8 is passed through line 11 to control valve 12, which permits the pressure to be reduced prior to the passage of the liquid effluent through line 13 to fractionation zone 14. In fractionation zone 14, the liquid is separated into benzene, toluene, xylenes, trimethylbenzenes and $C_{10}$ aromatics formed in reaction zone 5. Each of these streams is separated from one another in the fractionation zone. Benzene is removed by way of line 16, while toluene is taken from line 17 and the xylenes are removed by way of line 18. Unreacted trimethylbenzenes are removed from fractionation zone 14 by way of line 19. The trimethylbenzenes and toluene are recycled back to the reactor by line 17a. $C_{10}$ and $C_{10}+$ aromatics including tetramethylbenzenes are separated and sent to the gasoline pool by line 20.

The toluene in line 17 is conducted to line 4 where it joins the fresh feedstock from line 4 to be sent to reaction zone 5. Fresh toluene also can be admixed with reformate $C_9$ aromatics as fresh feed to the process.

Reaction conditions in reaction zone 5 are as follows: reaction temperatures range between approximately 600° to 1000° F., preferably between 800° to 900° F. The reaction is conducted at a pressure of from about 100 to about 500 psig, preferably 150 to 250 psig. Hydrogen to hydrocarbon mole ratios are within the range of 4:1 to 20:1, preferably 5:1 to 9:1 at pressures of 150 to 250 psig respectively. Space velocities are within the range of from about 0.1 to about 7 unit weights of hydrocarbon charge per weight of catalyst per hour (WHSV). Contact time can run from 1 to 20 second, preferably from 3 to 10 seconds. Feedstock concentrations can be varied, but maximum xylene yields can be obtained with feedstocks containing an average methyl group/benzene ring mole ratio of 1.4–2.1.

Embodiments of the process of the present invention may be found in the following examples. These embodiments and examples are presented for purposes of illustration only and are not intended to limit the scope of the invention.

EXAMPLES I–III

Heavy reformate fractions containing trimethylbenzenes, ethyltoluenes, propylbenzenes, tetramethylbenzenes and $C_{10}+$ aromatics were hydrodealkylated and transalkylated to xylenes, benzene and $C_2$–$C_4$ paraffins over an 800°–900° F. temperature.

The same feedstock was used in each example. It was made up of toluene, fractionated heavy reformate and hydrogen in such proportions so as to simulate an actual process reactor feed of heavy reformate (HR). The feedstock contained an average methyl group/benzene ring mole ratio of 1.4. Composition of this feedstock was as follows:

|  | Wt. % |
|---|---|
| Paraffins/naphthenes | 0.5 |
| $C_8$ aromatics | 0.3 |
| Toluene | 65.3 |
| Trimethylbenzenes | 23.6 |
| Ethyltoluenes | 6.7 |
| Propylbenzenes and Indane | 1.3 |
| Tetramethylbenzenes | 2.1 |
| $C_{10}+$ aromatics | 0.2 |

The catalyst consisted of 5% $MoO_3$/3% $WO_3$ on a gamma-alumina matrix containing 60% mordenite-H. The catalyst was crushed and used in a −20 to +40 mesh (U.S. Sieve) granular form. The B.E.T. surface area of the catalyst was 371 $m^2/g$.

Preparation of the catalyst was accomplished as follows. 2298.9 g of American Cyanamid sol, 9.5% $Al_2O_3$, was blended with 333.4 g of Norton Zeolon-H powdered mordenite sieve, in a Waring blender. The blend was gelled with 100 ml of a 50% $NH_4OH$ solution and dried overnight at 250° F. The dried material was then ground 20/40 mesh and calcined 3 hours at 1000° F.

460 g of the 20/40 mesh base was impregnated with a solution made by dissolving 30.3 g ammonium molybdate and 16.3 g ammonium metatung-state dissolved in 400 ml of distilled water. The sample was dried at 250° F. for 5 hours and calcined in air at 1000° F. for 3 hours. It was made to contain 5% $MoO_3$/3% $WO_3$ supported on 60% mordenite-H/40% $Al_2O_3$.

Prior to use, the catalyst was sulfided with hydrogen sulfide.

The reactor consisted of a tubular stainless steel pipe, 17 inches long, having an inner diameter (I.D.) of 0.5 inches. The reactor was heated by a constant temperature salt bath and the internal reactor temperature was measured by a movable thermocouple located in a thermowell along the reactor axis. Hydrogen and the hydrocarbon feed were metered into the reactor system through differential pressure cells. Separation of the liquid and gaseous product streams was made in a high pressure separator under system pressure. The liquid product was continuously withdrawn and collected under 3 psig pressure. The gaseous products were depressurized to 3 psig and sent directly to an on-line gas chromatograph.

Product samples were collected at intervals of at least 24 hours and analyzed by gas chromatography. The data are shown in Table I.

Table I

Transalkylation of Heavy Reformate-$C_9$ Aromatics; Feed:Methyl Group/Benzene Ring Mole Ratio of 1.4

| Example No. | I | II | III | Calculated Equilibrium Data |
|---|---|---|---|---|
| Conditions | | | | |
| Temperature, °F. | 800 | 850 | 900 | 800–900 |
| Pressure, psig | 172 | 172 | 172 | 172 |
| $H_2$/HC Mole Ratio | 6.2 | 6.1 | 6.1 | 6.0 |
| WHSV | 3.8 | 3.7 | 3.7 | — |
| Contact, seconds | 6.1 | 6.1 | 5.9 | — |
| Conversion, wgt. % | | | | |
| Toluene | 38.1 | 44.5 | 44.2 | 44.6 |
| Trimethylbenzenes | 50.9 | 53.3 | 51.3 | 48.2 |
| Ethyltoluenes | 74.9 | 90.8 | 94.9 | 100.0 |
| Propylbenzenes and Indane | 100.0 | 100.0 | 100.0 | 100.0 |
| Products | Yield, Wt. % | | | |
| Xylenes | 32.4 | 33.0 | 33.2 | 34.2 |
| Ethylbenzene | 0.9 | 0.4 | 0.2 | — |
| Benzene | 8.3 | 10.7 | 11.2 | 11.8 |
| Ethylxylenes | 0.4 | 0.2 | 0.1 | — |
| Paraffins/Naphthenes | | | | |
| Methane | 0.1 | 0.2 | 0.4 | — |
| Ethane | 1.0 | 2.6 | 2.9 | 1.7 |
| Propane | 0.9 | 2.4 | 1.6 | 0.5 |
| Butane | 0.3 | 0.7 | 0.4 | — |
| Pentane | 0.1 | 0.1 | 0.1 | — |
| Total | 2.6 | 6.3 | 5.4 | 2.2 |

Examples I, II and III illustrate the effectiveness of the process for concurrently hydrodealkylating the ethyltoluenes, propylbenzenes and indane, and trimethylalkylating the trimethylbenzenes and toluene contained in the reactor feed to benzene, xylenes and $C_2$–$C_4$ paraffins. The examples also show that the production of undesirable ethylaromatics such as ethylbenzene and ethylxylenes can be kept to a minimum with the process of this invention. The proximity of the xylene yields and reactant conversion levels with calculated equilibrium data is also illustrated in Table I. These examples illustrate the effectiveness of the process for achieving equilibrium yields and conversion levels.

As shown in Table I, xylene, benzene and $C_2$–$C_4$ paraffin yields, as well as the conversion of ethyltoluenes, can be increased by raising the temperature over the 800°–900° F. range.

EXAMPLES IV–VI

The conditions of Examples I–III were repeated, but with a reactor feed containing an average methyl group/benzene ring mole ratio of 2.1. Composition of this feedstock was as follows:

|  | Wt. % |
|---|---|
| Paraffins/Naphthenes | 0.5 |
| $C_8$ Aromatics | 0.4 |
| Toluene | 28.3 |
| Trimethylbenzenes | 46.6 |
| Ethyltoluenes | 11.6 |
| Propylbenzenes and Indane | 2.1 |
| Tetramethylbenzenes | 10.1 |
| $C_{10}+$ Aromatics | 0.4 |

The catalyst used in Examples IV–VI was previously described in Examples I–III. Results are in Table II.

Table II

Transalkylation of Heavy Reformate-$C_9$ Aromatics; Feed:Methyl Group/Benzene Ring Mole Ratio of 2.1

| Example No. | IV | V | VI | Calculated Equilibrium Data |
|---|---|---|---|---|
| Conditions | | | | |
| Temperature, °F. | 800 | 850 | 900 | 800–900 |
| Pressure, psig | 172 | 172 | 172 | 172 |
| $H_2$/HC Mole Ratio | 6.0 | 6.1 | 6.2 | 6.0 |
| WHSV | 4.4 | 4.2 | 4.0 | — |
| Contact, seconds | 6.0 | 6.0 | 6.0 | — |
| Conversion, wgt. % | | | | |
| Toluene | 33.9 | 33.6 | 32.0 | 34.3 |
| Trimethylbenzenes | 32.3 | 39.5 | 40.9 | 42.3 |
| Ethyltoluenes | 68.6 | 90.6 | 96.7 | 100.0 |
| Propylbenzenes and Indane | 100.0 | 100.0 | 100.0 | 100.0 |
| Products | | Yield, Wt. % | | |
| Xylenes | 29.3 | 35.2 | 36.0 | 36.8 |
| Ethylbenzene | 0.9 | 0.4 | 0.1 | — |
| Benzene | 2.3 | 3.0 | 3.2 | 3.0 |
| Ethylxylenes | 1.3 | 0.5 | 0.2 | — |
| Paraffins/Naphthenes | | | | |
| Methane | 0.1 | 0.2 | 0.5 | — |
| Ethane | 1.4 | 2.9 | 3.9 | 2.9 |
| Propane | 1.1 | 1.6 | 1.5 | 0.8 |
| Butane | 0.3 | 0.5 | 0.4 | — |
| Pentane | 0.1 | 0.1 | 0.1 | — |
| Total | 3.5 | 5.8 | 6.6 | 3.7 |

The data in Tables I and II indicate that the benzene yield is strongly dependent on the average methyl group/benzene ring ratio of the feed, i.e., decreasing the methyl group/benzene ring ratio from 2.1 to 1.4 increased the benzene yield from about 3 to 11 wt%. Thus, by controlling the methyl group/benzene ring ratio of the reactor feed, the production of benzene can be controlled in this hydrodealkylation/transalkylation process.

EXAMPLE VII

The feedstock used in Example VII simulates a process reactor feed that is based on a process fresh feed that does not contain any toluene. The composition of this feedstock was as follows:

| | Wt.% |
|---|---|
| paraffins/Naphthenes | 1.1 |
| $C_8$ Aromatics | 1.1 |
| Toluene | 21.4 |
| Trimethylbenzenes | 51.4 |
| Ethyltoluenes | 20.4 |
| Propylbenzenes and Indane | 3.6 |
| $C_{10}+$ Aromatics | 1.0 |

Although the process fresh feed does not contain any toluene, the reactor feed shown above does contain 21.4% toluene. This toluene is the recycle toluene generated in situ from the hydrodeethylation of the ethyltoluenes. Tetramethylbenzenes were omitted from the reactor feed, to simulate processing conditions whereby the tetramethylbenzenes would not be recycled. Results from processing this reactor feed over the catalyst described in Examples I–III, are summarized in Table III.

Table III

Transalkylation of Heavy Reformate-$C_9$ Aromatics With Recycle Toluene

| Example No. | VI | Calculated Equilibrium Data |
|---|---|---|
| Conditions | | |
| Temprature. °F. | 900 | 900 |
| Pressure, psig | 172 | 172 |
| $H_2$/HC Mole Ratio | 6.4 | 6.0 |
| WHSV | 2.6 | — |
| Contact, seconds | 8.9 | — |
| Converstion, wgt. % | | |
| Trimethylbenzenes | 56.9 | 56.7 |
| Ethyltoluenes | 98.0 | 100.0 |
| Propylbenzenes and Indane | 100.0 | 100.0 |
| Products | Yield, Wt. % | |
| Xylenes | 34.2 | 35.6 |
| Ethylbenzene | 0.1 | — |
| Benzene | 4.4 | 4.2 |
| Ethylxylenes | 0.1 | — |
| Tetramethylbenzenes | 3.4 | 7.6 |
| Paraffins/Naphthenes | | |
| Methane | 0.7 | — |
| Ethane | 6.4 | 5.2 |
| Propane | 2.5 | 1.7 |
| Butane | 0.6 | — |
| Pentane | 0.1 | — |
| Total | 10.8 | 6.9 |

What is claimed is:

1. A process for producing ethylbenzene-lean xylenes, benzene, and $C_2$–$C_4$ paraffins wherein a $C_9$-aromatics stream comprising trimethylbenzenes, ethyltoluenes, propylbenzenes, indane and $C_{10}$ paraffins/naphthenes is fractionated from heavy reformate, mixed with a hydrogen-affording gas, and subjected to a hydrodealkylation/transalkylation reaction under conditions including a temperature within the range of from 600° to about 1000° F., a pressure in the range of from about 100 to 500 psig, a hydrogen-to-hydrocarbon mole ratio of from about 4:1 to 20:1, a contact time of from about 1 to 20 seconds and a catalyst composition consisting essentially of a tungsten/molybdenum component of $WO_3$ and $MoO_3$ with an acidic component of mordenite on a high surface area alumina support.

2. The process of claim 1 wherein the said tungsten/molybdenum component comprises tungsten being present in an amount within the range of from about 1 to 10 (wt) percent expressed as $WO_3$ and molybdenum being present in an amount within the range of from about 1 to 20 (wt.)%, expressed as $MoO_3$ and based upon the weight of the catalytic composition.

3. The process of claim 1 wherein the said acidic component of mordenite and high surface area alumina comprises the said mordenite being present in an amount within the range of from 5 to about 95 (wt.)% and the catalytically active alumina being present in an amount within the range of from 95 to 5 (wt.)%.

4. The process of claim 1 wherein the said catalyst composition comprises a tungsten/molybdenum component of 3 (wt.)% $WO_3$ and 5 (wt.)% $MoO_3$ of total weight of said catalytic composition and an acidic component comprising 60 (wt.)% mordenite and 40 (wt.)% catalytically active alumina of total weight of said acidic cracking component.

5. The process of claim 4 wherein the said mordenite is in the hydrogen form and the said alumina is gamma alumina.

6. The process of claim 1 wherein said catalyst composition comprises the sulfided form.

7. The process of claim 1 wherein the said reaction products are separated from unreacted feedstocks.

8. The process of claim 1 wherein the toluene is admixed with reformate $C_9$ aromatics as the fresh feed to the process.

9. The process of claim 1 wherein the said hydrogen-to-hydrocarbon mole ratio is from about 5:1 to 9:1 at pressures of from about 150 to 250 psig respectively.

10. The process of claim 1 wherein the said contact time is from 3 to 10 seconds.

11. The process of claim 1 wherein the said temperature is within the range from about 800° to 900° F.

* * * * *

UNITED STATES PATENT OFFICE
CERTIFICATE OF CORRECTION

Patent No. 4,172,813          Dated October 30, 1979

Inventor(s) Allen I. Feinstein and Ralph J. Bertolacini

It is certified that error appears in the above-identified patent and that said Letters Patent are hereby corrected as shown below:

| Patent Column | Line | |
|---|---|---|
| 1 | 11 | "cooking" should be --coking-- |
| 1 | 18 | "However, derived," should be --However derived, |
| 3 | 15 | "1200°F. pressure" should be --1200°F. and pressure-- |
| 4 | 37 | "hydroadealkylation" should be --hydrodealkylation-- |
| 5 | 41 | "process" should be --processes-- |
| 6 | 68 | "suitably" should be --suitable-- |
| 7 | 21 | "Group 1Vb" should be --Group Vlb-- |
| 8 | 16-17 | "$C_9$ hydrogen" should be --$C_9$ hydrocarbon-- |
| 9 | 47 | "metatung-state" should be --metatungstate-- |

Signed and Sealed this

Fifth Day of August 1980

[SEAL]

Attest:

SIDNEY A. DIAMOND

Attesting Officer      Commissioner of Patents and Trademarks